United States Patent [19]
Kiefer et al.

[11] Patent Number: 5,620,867
[45] Date of Patent: Apr. 15, 1997

[54] BONE MORPHOGENETIC PROTEIN EXPRESSION AND DNA

[75] Inventors: Michael C. Kiefer, Clayton; Frank R. Masiarz, San Francisco; Philip J. Barr, Oakland, all of Calif.

[73] Assignee: Chiron Corporation, Emeryville, Calif.

[21] Appl. No.: 142,847

[22] Filed: Oct. 26, 1993

Related U.S. Application Data

[63] Continuation of Ser. No. 819,662, Jan. 13, 1992, abandoned, which is a continuation of Ser. No. 382,805, Jul. 19, 1989, abandoned.

[51] Int. Cl.$^6$ .......................... C12N 15/18; C12N 15/11; C12N 5/10; C12N 15/63
[52] U.S. Cl. ...................... 435/69.4; 435/69.8; 435/69.9; 435/240.1; 435/320.1; 536/23.1; 536/23.4; 536/23.51
[58] Field of Search .................................. 435/69.1, 69.9, 435/172.3, 235.1, 320.1, 240.1, 255, 256, 252.3, 69.4; 536/23.1, 23.51, 23.4; 530/350; 935/9, 27, 31, 32, 34, 38, 55, 69, 70, 72

[56] References Cited

U.S. PATENT DOCUMENTS

| | | | |
|---|---|---|---|
| 4,294,753 | 10/1981 | Urist | 530/395 |
| 4,394,370 | 7/1983 | Jefferies | 424/15 |
| 4,434,094 | 2/1984 | Seyedin et al. | 530/416 |
| 4,455,256 | 6/1984 | Urist | 530/350 |
| 4,526,909 | 7/1985 | Urist | 523/115 |
| 4,546,082 | 10/1985 | Kuojan et al. | 435/172.3 |
| 4,563,489 | 1/1986 | Urist | 524/21 |
| 4,596,574 | 6/1986 | Urist | 623/16 |
| 4,619,989 | 10/1986 | Urist | 530/417 |
| 4,627,982 | 12/1986 | Seyedin et al. | 424/95 |
| 4,761,471 | 8/1988 | Urist | 530/350 |
| 4,795,804 | 1/1989 | Urist | 530/350 |
| 4,804,744 | 2/1989 | Sen | 530/350 |
| 4,810,691 | 3/1989 | Seyedin et al. | 514/2 |
| 5,013,649 | 5/1991 | Wang et al. | 435/69.1 |

FOREIGN PATENT DOCUMENTS

| | | |
|---|---|---|
| 0148155 | of 0000 | European Pat. Off. . |
| 0289314 | of 0000 | European Pat. Off. . |
| 0336760 | of 0000 | European Pat. Off. . |
| 2164042 | of 0000 | United Kingdom . |
| WO88/00205 | of 0000 | WIPO . |
| 8910409 | 11/1989 | WIPO . |

OTHER PUBLICATIONS

Burnett, et al., Chemical Abstracts, vol. 111, No. 9, Aug. 1989.
Sampath, et al., Calcified Tissue Int'l, Suppl 2, vol. 46, Apr. 1990.
Wang et al., Proceedings of the National Academy of Science of USA, vol. 85, Dec. 1988.
Urist, "Bone: Formation by Autoinduction," Science (1965), 150:893–899.
Urist, "A bone matrix calcification–initiator noncollagenous protein," Am. J. Physiol. (1977), 232:C115–C127.
Bauer et al., "Human Osteosarcoma–Dervied Soluble Bone Morphogenetic Protein," Clin. Ortho. (1981), 154:291–295.
Conover et al., "Dentin Matrix Bone Morphogenetic Protein," ed. by Arthur Vels in Chem. Biol. Min. Corr. Tissue, (1981), pp. 597–606.
Urist et al., "A bovine low Molecular Weight Bone Morphogenetic Protein (BMP) Fraction," Clin. Ortho. (1981), 126:219–232.
Urist et al., "Bone Cell Differentiation and Growth Factors," Science, (1983), 220:680–686.
Urist et al., "Human Bone Morphogenetic Protein," Proc. Soc. Exp. Biol. Med. (1983), 173:194–199.
Sato et al., "Bone Morphogenetic Protein–induced Cartilage Development in Tissue Culture," Clin. Ortho. (1984), 183:180–187.
Urist et al., "Purification of bovine bone morphogenetic Protein by Hydroxy–apatite Chromatography," Proc. Natl. Acad. Sci. USA (1984), 81:371–375.
Urist et al., "Preparation and Bioassy of Bone Morphogenetic Protein and Polypeptide Fragments," Barnes and Sirbaska, eds. in Meth. Enzymol. (1987), 146:294–312.
Kawamura et al., "Growth Factors, Mitogens, Cytokines, and Bone Morphogenetic Protein in Induced Chondrogenesis in Tissue Culture," Develop. Biol. (1988), 130:435–442.
Kawai et al., "Quantitative Computation of Induced Heterotopic Bone Formation by an Image Analysis System," Clin. Ortho. (1988), 233:262–267.
Termine et al., "Mineral and Collagen–binding Proteins of Fetal Calf Bone," J. Biol. Chem. (1981), 256:10403–10408.
Luyten et al., "Purification and Partial Amino Acid Sequence of Osteogenin, a Protein Initiating Bone Differentiation" J. Biol. Chem. (1989) 264:13377–13380.
Wozney et al., "Novel Regulators of Bone Formation: Molecular Clones and Activities," Science (1988), 242:1528–1534.
Siggs et al Proc. Natl Acad Sci USA vol. 78 pp. 6613–6617 (1981).
Maniatis et al Molecular Cloning: A Laboratory Manual Cold Spring Harbor Laboratory, CSH, NY (1982) pp. 404–433.

*Primary Examiner*—Stephen G. Walsh
*Assistant Examiner*—Robert C. Hayes
*Attorney, Agent, or Firm*—Ling-Fong Chung; Paul B. Savereide; Robert P. Blackburn

[57] ABSTRACT

The purification and cloning of bone morphogenetic proteins are disclosed, as well as production of BMP and its analogs thereof by recombinant DNA techniques. Pharmaceutical compositions comprising BMP and the use of such compositions are also disclosed.

18 Claims, 6 Drawing Sheets

FIG. 1

```
        PEPTIDE A
        VAL ASN ALA LEU ASP GLU ASP SER LEU THR MET ASP LEU GLU PHE ARG
        PROBE A
    5'  GTG AAT GCC CTG GAT GAG GAC TCC CTG ACC ATG GAC CTG GAG TTC CG  3'
                     T                   T           T T

5'  GTG AAT GCC CTG GAT GAG GAC AGC CTG ACC ATG GAC CTG GAG TTC CG  3'
                     T                   T           T T

PEPTIDE B
        GLU SER GLU ALA ASP PRO ALA THR CYS ASP PHE GLN ARG
        PROBE B
    5'  GAG TCC GAG GCT GAC CCT GCC ACC TGC GAC TTC CAA CG  3'
                                         T   T   T   G

5'  GAG AGC GAG GCT GAC CCT GCC ACC TGC GAC TTC CAA CG  3'
                                         T   T   T   G

PEPTIDE C
        MET SER ALA GLU GLN VAL GLN ASN VAL TRP VAL ARG
        PROBE C
    5'  ATG TCT GCT GAA CAA GTG CAA AAC GTC TGG GTG CG  3'
                         G   G       G   T

5'  ATG AGT GCT GAA CAA GTG CAA AAC GTC TGG GTG CG  3'
                         G   G       G   T

PEPTIDE D
        GLY TYR HIS VAL PRO VAL ALA VAL CYS ARG
        PROBE D
    5'  GGC TAC CAC GTG CCT GTG GCT GTC TGC AG  3'
             T   T                       T C
```

ADDITIONAL TRYPTIC PEPTIDES

PEPTIDE E
GLY GLU PRO LEU TYR GLU PRO SER ARG

PEPTIDE F
GLU ALA LEU SER ALA SER VAL ALA LYS

PEPTIDE G
VAL ASN SER GLN SER LEU SER PRO TYR

PEPTIDE H
ASN SER TYR LEU LEU GLY LEU THR PRO ASP ARG

FIG. 2A

TWO BOVINE BMP EXONS

```
                                        PEPTIDE A
   ArgProLeuProLeuValPheLeuLys ValAsnAlaLeuAspGluAspSerLeuThrMet
  ThrProLeuAlaProCysPheSerGlu GlyGlnArgProGlyArgGlyGlnLeuAspHis
  AsnAlaProCysProLeuPhePheOP  ArgSerThrProTrpThrArgThrAlaOP Pro
.. AACGCCCCTTGCCCCTTGTTTTTCTGAA GTCAACGCCCTGGACGAGGACAGCTTGACCA
.. TTGCGGGGAACGGGGAACAAAAAGACTT CAGTTGCGGGACCTGCTCCTGTCGAACTGGT
                                                    PEPTIDE B
   AspLeuGluPheArg IleGlnGluThrThrCysArgArg GluSerGluAlaAspProAla      EXON
   GlyLeuArgValGlnAspSerArgAspAspValGlnGluGlyIleOP GlyArgProArg         3
   TrpThrAM SerSerGlyPheLysArgArgArgAlaGlyGlyAsnLeuArgGlnThrPro
   TGGACTTAGAGTTCAGGA TTCAAGAGACGACGTGCAGGAGGGAATCTGAGGCAGACCCCG
   ACCTGAATC TCAAGTCCTAAGTTCTCTGCTGCACGTCCTCCCTTAGACTCCGTCTGGGGC
              PEPTIDE D
    ThrCysAspPheGlnArg GlyTyrHisVal ValSerValGlyGlnArgProProAlaTrp
    HisLeuOP LeuProGluGlyLeuProArg GlyGluCysGlyAlaLysAlaThrSerLeu
    ProProValThrSerArgGlyAlaThrThrTrp OP ValTrpGlyLysGlyHisGlnPro
    CCACCTGTGACTTCCAGAGGGGCTACCACGTG GTGAGTGTGGGGCAAAGGCCACCAGCCT...
    GGTGGACACTGAAGGTCTCCCCGATGGTGCAC CACTCACACCCCGTTTCCGGTGGTCGGA...
```

FIG. 2B

```
                                        PEPTIDE D
   SerSerProPheLeuLeuPheGln ProValAlaValCysArg SerThrValArg MetSer
   GluLeuThrIleSerProPhePro AlaArgGlyArgLeuGlnLysHisArgAlaAspVal
   GlyAlaHisHisPheSerPheSerSer ProTrpProPheAlaGluAlaProCysGlyCys
...GGAGCTCACCATTTCTCCTTTTCCAG CCCGTGGCCGTTTGCAGAAGCACCGTGCGGATGT
...CCTCGAGTGGTAAAGAGGAAAAGGTC GGGCACCGGCAAACGTCTTCGTGGCACGCCTACA
               PEPTIDE C                                                EXON
     AlaGluGlnValGlnAsnValTrpValArg CysHisTrpSerSerSerSerGlySerSer       4
     CysOP ThrGlyAlaGluArgValGlySerLeuProLeuValLeuGlnLeuTrpValGln
     LeuLeuAsnArgCysArgThrCysGlyPheAlaAlaThrGlyProProAlaLeuGlyPro
     CTGCTGAACAGGTGCAGAACGTGTGGGTTCGCTGCCACTGGTCCTCCAGCTCTGGGTCCA
     GACGACTTGTCCACGTCTTGCACACCCAAGCGACGGTGACCAGGAGGTCGAGACCCAGGT

SerSerGluGlu ValCysThrGlyAlaCysThrGlyValHisArgTyrAlaProHisPro
     GlnGlnOP Arg GlyMetHisGlyGlyLeuHisArgCysAlaGlnValCysThrProSer
     AlaAlaValLysArg TyrAlaArgGlyLeuAlaGlnValCysThrGlyMetHisProIle
     GCAGCAGTGAAGAG GTATGCACGGGGGCTTGCACAGGTGTGCACAGGTATGCACCCCATC...
     CGTCGTCACTTCTC CATACGTGCCCCCGAACGTGTCCACACGTGTCCATACGTGGGGTAG...
```

FIG. 3

BOVINE BMP cDNA

```
TGATAAACAGCTGCTTTCAGGACAACTGGTCAGCCCCAAAGGCACACAGACAATCTCCCT
ACTATTTGTCGACGAAAGTCCTGTTGACCAGTCGGGGTTTCCGTGTGTCTGTTAGAGGGA
                              -23
                                    MetGluLysMetAlaMetLysMetLeuVal
ATCTCTGGCACGGAAATTGTTCTTCCCATAATGGAGAAGATGGCGATGAAGATGTTGGTG
TAGAGACCGTGCCTTTAACAAGAAGGGTATTACCTCTTCTACCGCTACTTCTACAACCAC
                                                    -1 ↓ +1
IlePheValLeuGlyMetAsnHisTrpThrCysThrGlyPheProValTyrAspTyrAsp
ATATTTGTCCTTGGAATGAACCACTGGACTTGTACAGGTTTCCCGGTGTATGACTATGAC
TATAAACAGGAACCTTACTTGGTGACCTGAACATGTCCAAAGGGCCACATACTGATACTG

ProAlaSerLeuLysGluAlaLeuSerAlaSerValAlaLysValAsnSerGlnSerLeu
CCGGCTTCCCTGAAGGAGGCTCTCAGCGCCTCTGTGGCAAAAGTGAATTCCCAGTCACTG
GGCCGAAGGGACTTCCTCCGAGAGTCGCGGAGACACCGTTTTCACTTAAGGGTCAGTGAC

SerProTyrLeuPheArgAlaPheArgSerSerValLysArgValAsnAlaLeuAspGlu
AGCCCCTATCTGTTTCGGGCGTTTAGAAGCTCAGTTAAAAGAGTCAACGCCCTGGACGAG
TCGGGGATAGACAAAGCCCGCAAATCTTCGAGTCAATTTTCTCAGTTGCGGGACCTGCTC

AspSerLeuThrMetAspLeuGluPheArgIleGlnGluThrThrCysArgArgGluSer
GACAGCTTGACCATGGACTTAGAGTTCAGGATTCAAGAGACGACGTGCAGGAGGGAATCT
CTGTCGAACTGGTACCTGAATCTCAAGTCCTAAGTTCTCTGCTGCACGTCCTCCCTTAGA

GluAlaAspProAlaThrCysAspPheGlnArgGlyTyrHisValProValAlaValCys
GAGGCAGACCCCGCCACCTGTGACTTCCAGAGGGGCTACCACGTGCCCGTGGCCGTTTGC
CTCCGTCTGGGGCGGTGGACACTGAAGGTCTCCCCGATGGTGCACGGGCACCGGCAAACG

ArgSerThrValArgMetSerAlaGluGlnValGlnAsnValTrpValArgCysHisTrp
AGAAGCACCGTGCGGATGTCTGCTGAACAGGTGCAGAACGTGTGGGTTCGCTGCCACTGG
TCTTCGTGGCACGCCTACAGACGACTTGTCCACGTCTTGCACACCCAAGCGACGGTGACC

SerSerSerSerGlySerSerSerSerGluGluMetPhePheGlyAspIleLeuGlySer
TCCTCCAGCTCTGGGTCCAGCAGCAGTGAAGAGATGTTTTTTGGGGATATCTTGGGATCC
AGGAGGTCGAGACCCAGGTCGTCGTCACTTCTCTACAAAAAACCCCTATAGAACCCTAGG

SerThrSerArgAsnSerTyrLeuLeuGlyLeuThrProAspArgSerArgGlyGluPro
TCTACATCAAGAAACAGTTACCTGCTTGGCCTCACTCCTGACAGATCCAGAGGTGAACCA
AGATGTAGTTCTTTGTCAATGGACGAACCGGAGTGAGGACTGTCTAGGTCTCCACTTGGT

LeuTyrGluProSerArgGluMetArgArgAsnPheProLeuGlyAsnArgArgTyrSer
CTTTATGAACCATCACGTGAGATGAGAAGAAACTTTCCTCTTGGAAATAGAAGGTACTCG
GAAATACTTGGTAGTGCACTCTACTCTTCTTTGAAAGGAGAACCTTTATCTTCCATGAGC
                                                      180
AsnProTrpProArgAlaArgValAsnProGlyPheGluOP
AACCCGTGGCCCAGAGCAAGAGTAAACCCTGGCTTTGAGTGACAGCCTTAAGCAAAATGC
TTGGGCACCGGGTCTCGTTCTCATTTGGGACCGAAACTCACTGTCGGAATTCGTTTTACG

ACTGGAAGGAATAGAAGTTCCAATGAAGAAAGATACCTTATGAATTGTGTAATTTTCTTT
TGACCTTCCTTATCTTCAAGGTTACTTCTTTCTATGGAATACTTAACACATTAAAAGAAA

TGATCAATTGCAGTCCCTAATAAATGGCTTACTTTTCC
ACTAGTTAACGTCAGGGATTATTTACCGAATGAAAGG
```

FIG. 4A

```
                                          CTCTTAGGAAGAACTGTCA
                                          GAGAATCCTTCTTGACAGT

MetIleSerArgMet
TCCCCAAACACATAGAGAGACACTCTCTGTCTCTCGATTACAATCATGATTTCCAGAATG        EXON
AGGGGTTTGTGTATCTCTCTGTGAGAGACAGAGAGCTAATGTTAGTACTAAAGGTCTTAC          1

GluLysMetThrMetMetMetLysIleLeuIleMetPheAlaLeuGlyMetAsnTyrTrp
GAGAAGATGACGATGATGATGAAGATATTGATTATGTTTGCTCTTGGAATGAACTACTGG
CTCTTCTACTGCTACTACTACTTCTATAACTAATACAAACGAGAACCTTACTTGATGACC

SerCysSerGly
TCTTGCTCAGGTAAGGTATTCACCAACCTGGCCACCTGCTCTGGATCATGCAGAGCCATG
AGAACGAGTCCATTCCATAAGTGGTTGGACCGGTGGACGAGACCTAGTACGTCTCGGTAC

GlyPheProVal
CTGGCGCCTGTGTCTTGTCTCACTGTGCCCCATGTGCTTGCGTGTCCAGGTTTCCCAGTG       EXON
GACCGCGGACACAGAACAGAGTGACACGGGGTACACGAACGCACAGGTCCAAAGGGTCAC         2

TyrAspTyrAspProSerSerLeuArgAspAlaLeuSerAlaSerValValLysValAsn
TACGACTACGATCCATCCTCCTTAAGGGATGCCCTCAGTGCCTCTGTGGTAAAAGTGAAT
ATGCTGATGCTAGGTAGGAGGAATTCCCTACGGGAGTCACGGAGACACCATTTTCACTTA

SerGlnSerLeuSerProTyrLeuPheArgAlaPheArgSerSerLeuLysArg
TCCCAGTCACTGAGTCCGTATCTGTTTCGGGCATTCAGAAGCTCATTAAAAAGAGTAAGT
AGGGTCAGTGACTCAGGCATAGACAAAGCCCGTAAGTCTTCGAGTAATTTTTCTCATTCA

GCAAAATGAAATCTTCTCTACTCCTCCTTCCAATGCTGTCT
CGTTTTACTTTAGAAGAGATGAGGAGGAAGGTTACGACAGA
```

FIG. 4B-1

```
                                                          Val
ATAGCATCATAAACTTCAGAAATGCATTGATCACACTCTGAAACTTTATTTTTGTGAAGG
TATCGTAGTATTTGAAGTCTTTACGTAACTAGTGTGAGACTTTGAAATAAAAACACTTCC        EXON
                                                                      3
GluValLeuAspGluAsnAsnLeuValMetAsnLeuGluPheSerIleArgGluThrThr
TTGAGGTCCTAGATGAGAACAACTTGGTCATGAATTTAGAGTTCAGCATCCGGGAGACAA
AACTCCAGGATCTACTCTTGTTGAACCAGTACTTAAATCTCAAGTCGTAGGCCCTCTGTT

CysArgLysAspSerGlyGluAspProAlaThrCysAlaPheGlnArgAspTyrTyrVal
CATGCAGGAAGGATTCTGGAGAAGATCCCGCTACATGTGCCTTCCAGAGGGACTACTATG
GTACGTCCTTCCTAAGACCTCTTCTAGGGCGATGTACACGGAAGGTCTCCCTGATGATAC

TGGTAAGTGGGAGGAGACCCATCCCAGAAATGAACAAAAGGAAGAGCCTCACTTCTTCCA
ACCATTCACCCTCCTCTGGGTAGGGTCTTTACTTGTTTTCCTTCTCGGAGTGAAGAAGGT
```

FIG. 4B-2

```
                                           SerThrAlaValCysArgSerThr        EXON
CAGCTGAAGAGAGAACTCACCCCTTTGTCTTTTCCAGTCCACAGCTGTTTGCAGAAGCACC               4
GTCGACTTCTCTCTTGAGTGGGGAAACAGAAAAGGTCAGGTGTCGACAAACGTCTTCGTGG

ValLysValSerAlaGlnGlnValGlnGlyValHisAlaArgCysSerTrpSerSerSer
GTGAAGGTATCTGCCCAGCAGGTGCAGGGCGTGCATGCTCGCTGCAGCTGGTCCTCCTCC
CACTTCCATAGACGGGTCGTCCACGTCCCGCACGTACGAGCGACGTCGACCAGGAGGAGG

ThrSerGluSerTyrSerSerGluGlu
ACGTCTGAGTCTTACAGCAGCGAAGAGGTATGACTGGGGCCTTG
TGCAGACTCAGAATGTCGTCGCTTCTCCATACTGACCCCGGAAC
```

FIG. 4C-1

```
                                                     MetIlePheGly           EXON
TTTTCTTTCTTTCATGTGCTGACACATCCTGATGCCTGAATTTCTTTAGATGATTTTTGGG              5
AAAAGAAAGAAAGTACACGACTGTGTAGGACTACGGACTTAAAGAAATCTACTAAAAACCC

AspMetLeuGlySerHisLysTrpArgAsnAsnTyrLeuPheGly
GACATGTTGGGATCTCATAAATGGAGAAACAATTATCTATTTGGTAAGTTAAGACCCCG
CTGTACAACCCTAGAGTATTTACCTCTTTGTTAATAGATAAACCATTCAATTCTGGGGC
```

FIG. 4C-2

```
                                           GlyLeuIleSerAspGluSerIle         EXON
GAGAGGAGTCTTGTCTTATGATTATTACTGTGTTACAGGTCTCATTTCAGACGAGTCCAT               6
CTCTCCTCAGAACAGAATACTAATAATGACACAATGTCCAGAGTAAAGTCTGCTCAGGTA

SerGluGlnPheTyrAspArgSerLeuGly
AAGTGAACAATTTTATGATCGGTCACTTGGTAAGTGATTTCTTTCCTGCTGTGCCACCAG
TTCACTTGTTAAAATACTAGCCAGTGAACCATTCACTAAAGAAAGGACGACACGGTGGTC
```

FIG. 4C-3

```
                                            GlyIleMetArgArg                 EXON
GATCTTGATGTGACTGACAGAGCCTATGCTTCCCTTTTCTATCTTTAGGGATCATGAGAAGG            7
CTAGAACTACACTGACTGTCTCGGATACGAAGGGAAAAGATAGAAATCCCTAGTACTCTTCC

ValLeuProProGlyAsnArgArgTyrProAsnHisArgHisArgAlaArgIleAsnThr
GTATTGCCTCCTGGAAACAGAAGGTACCCAAACCACCGGCACAGAGCAAGAATAAATACT
CATAACGGAGGACCTTTGTCTTCCATGGGTTTGGTGGCCGTGTCTCGTTCTTATTTATGA

AspPheGluOC
GACTTTGAGTAACGGCCTTGAGGTAAGAAAATGCAGGTGCACACAAGTGTATTTAGAA
CTGAAACTCATTGCCGGAACTCCATTCTTTTACGTCCACGTGTGTTCACATAAATCTT
```

FIG. 5

HUMAN BMP cDNA

```
-29
        MetIleSerArgMetGluLysMetThrMetMetMetLysIleLeuIleMetPhe
    ACAATCATGATTTCCAGAATGGAGAAGATGACGATGATGATGAAGATATTGATTATGTTT
    TGTTAGTACTAAAGGTCTTACCTCTTCTACTGCTACTACTACTTCTATAACTAATACAAA
                         -1 ↓ +1
    AlaLeuGlyMetAsnTyrTrpSerCysSerGlyPheProValTyrAspTyrAspProSer
    GCTCTTGGAATGAACTACTGGTCTTGCTCAGGTTTCCCAGTGTACGACTACGATCCATCC
    CGAGAACCTTACTTGATGACCAGAACGAGTCCAAAGGGTCACATGCTGATGCTAGGTAGG

SerLeuArgAspAlaLeuSerAlaSerValValLysValAsnSerGlnSerLeuSerPro
    TCCTTAAGGGATGCCCTCAGTGCCTCTGTGGTAAAAGTGAATTCCCAGTCACTGAGTCCG
    AGGAATTCCCTACGGGAGTCACGGAGACACCATTTTCACTTAAGGGTCAGTGACTCAGGC

TyrLeuPheArgAlaPheArgSerSerLeuLysArgValGluValLeuAspGluAsnAsn
    TATCTGTTTCGGGCATTCAGAAGCTCATTAAAAAGAGTTGAGGTCCTAGATGAGAACAAC
    ATAGAGAAAGCCCGTAAGTCTTCGAGTAATTTTTCTCAACTCCAGGATCTACTCTTGTTG

LeuValMetAsnLeuGluPheSerIleArgGluThrThrCysArgLysAspSerGlyGlu
    TTGGTCATGAATTTAGAGTTCAGCATCCGGGAGACAACATGCAGGAAGGATTCTGGAGAA
    AACCAGTACTTAAATCTCAAGTCGTAGGCCCTCTGTTGTACGTCCTTCCTAAGACCTCTT

AspProAlaThrCysAlaPheGlnArgAspTyrTyrValSerThrAlaValCysArgSer
    GATCCCGCTACATGTGCCTTCCAGAGGGACTACTATGTGTCCACAGCTGTTTGCAGAAGC
    CTAGGGCGATGTACACGGAAGGTCTCCCTGATGATACACAGGTGTCGACAAACGTCTTCG

ThrValLysValSerAlaGlnGlnValGlnGlyValHisAlaArgCysSerTrpSerSer
    ACCGTGAAGGTATCTGCCCAGCAGGTGCAGGGCGTGCATGCTCGCTGCAGCTGGTCCTCC
    TGGCACTTCCATAGACGGGTCGTCCACGTCCCGCACGTACGAGCGACGTCGACCAGGAGG

SerThrSerGluSerTyrSerSerGluGluMetIlePheGlyAspMetLeuGlySerHis
    TCCACGTCTGAGTCTTACAGCAGCGAAGAGATGATTTTTGGGGACATGTTGGGATCTCAT
    AGGTGCAGACTCAGAATGTCGTCGCTTCTCTACTAAAAACCCCTGTACAACCCTAGAGTA

LysTrpArgAsnAsnTyrLeuPheGlyLeuIleSerAspGluSerIleSerGluGlnPhe
    AAATGGAGAAACAATTATCTATTTGGTCTCATTTCAGACGAGTCCATAAGTGAACAATTT
    TTTACCTCTTTGTTAATAGATAAACCAGAGTAAAGTCTGCTCAGGTATTCACTTGTTAAA

TyrAspArgSerLeuGlyIleMetArgArgValLeuProProGlyAsnArgArgTyrPro
    TATGATCGGTCACTTGGGATCATGAGAAGGGTATTGCCTCCTGGAAACAGAAGGTACCCA
    ATACTAGCCAGTGAACCCTAGTACTCTTCCCATAACGGAGGACCTTTGTCTTCCATGGGT
                                                            182
    AsnHisArgHisArgAlaArgIleAsnThrAspPheGluOC
    AACCACCGGCACAGAGCAAGAATAAATACTGACTTTGAGTAACGGCCTTGAGGT
    TTGGTGGCCGTGTCTCGTTCTTATTTATGACTGAAACTCATTGCCGGAACTCCA
```

5,620,867

BONE MORPHOGENETIC PROTEIN EXPRESSION AND DNA

This application is a continuation, of application Ser. No. 07/819,662, filed 13 Jan. 1992, now abandoned which is a continuation of Ser. No. 07/382,805, filed on 19 Jul. 1989 now abandoned.

This invention relates to a bone morphogenetic protein (BMP) which initiates cartilage and bone growth. The full length coding sequence for BMP, a polypeptide, is provided. The BMP is provided by isolation from bone sources and by synthesis using recombinant DNA techniques.

BACKGROUND OF THE INVENTION

It is known that demineralized bone matrix induces new bone formation when implanted in the soft tissue by a process generally designated as matrix induced bone formation (see Urist, M. R., Science, 150: 893–899 (1965)). There have been numerous efforts to extract and identify the active material (or materials) which induces this process, and it has been generally referred to in the literature as bone morphogenetic protein(s) (BMP). It is uncertain whether BMP is a single material or a mixture of materials, and there does not appear to be agreement among the investigators as to which material, if any, is the bone morphogenetic protein. As discussed herein, the term BMP is used to describe the protein having the amino acid sequence shown in FIG. 3 (bovine BMP) or FIG. 5 (human BMP), without the signal peptide.

The therapeutic use of BMP offers considerable advantages over use of traditional bone graft materials. While not intended to be limited by any theory, one hypothesis assumes that BMP initiates the differentiation of tissue cells into osteoblasts (cells that manufacture bone). During a process that replicates normal human fetal development, BMP-induced osteoblasts form cartilage which, over a period of several weeks yields solid bone. Thus BMP may be useful for replacing bone that has been destroyed by disease or accident, for use in treatment of scoliosis victims, for treatment of mal- or mis-formed bone, for use in healing of a fracture, dental reconstruction, hip replacement, bone remodeling, and control of osteoporosis.

It is thus an object of the present invention to produce a functional cartilage and bone growth factor or a component thereof, which is a protein identified by its entire amino acid sequence, which has BMP activity.

It is another object of the present invention to produce this biologically active BMP protein by recombinant DNA technology.

SUMMARY OF THE INVENTION

The present invention provides a class of mature native mammalian proteins termed herein as "bone morphogenetic protein" or "BMP", exemplified by the native human and bovine BMP sequences described herein. Generally, this class of proteins induce bone growth in vivo or in vitro. The human and/or bovine BMP sequences are representative of the class, and can be used to identify and isolate other mammalian BMP proteins, which will be at least partially or substantially homologous in nucleotide and amino acid sequences. Those of skill in the art will be able to readily identify other mammalian BMP's based on sequence homology to the human and bovine proteins disclosed herein, as well as biological activity. It is recognized that there may be allelic variations in BMP within a species, and such allelic variants are also within the scope of the class of proteins provided by the present invention.

The present invention further provides polypeptides which are analogs of BMP, such as BMP muteins, fusion proteins comprising BMP or BMP domains, and BMP fragments. Preferred analogs have BMP activity. A BMP mutein is a protein substantially homologous to a native BMP sequence (e.g., a minimum of about 75%, 85%, 90% or 95% homologous) wherein at least one amino acid is different. The term fusion protein includes a protein comprising a complete BMP sequence or a BMP domain, and a heterologous N- or C-terminal sequence (such as a signal sequence or sequence which protects the protein from degradation). A BMP fragment or domain is an amino acid sequence of sufficient length from a BMP protein such that it is identifiable as having been derived from such BMP protein. The origin of a particular peptide can be determined, for example by comparing its sequence to those in public databases.

The present invention provides in another embodiment BMP having amino acid sequence shown in FIGS. 3 and 5 (which also show the signal peptide). The present invention also provides methods of preparing the BMP by recombinant DNA techniques.

In yet another embodiment, the present invention provides the DNA sequence encoding BMP or analogs thereof, which may be used to construct vectors for expression in host systems by recombinant DNA techniques.

In still another embodiment, the present invention provides therapeutic compositions comprising BMP and, optionally, other osteoinductive associated factors such as matrix Gla protein (MGP) and bone calcification factor (BCF) and methods for forming cartilage and bone in vertebrates by introducing in vivo at the desired site an effective bone initiating amount of BMP. The identity of MGP was first reported by Price, Urist and Otawara in *Biochem. Biophys. Res. Comm.* 117:765–771 (1983). The identity of BCF is disclosed in commonly assigned copending Ser. No. 360,826, filed Jun. 2, 1989.

BRIEF DESCRIPTION OF THE DRAWINGS

FIG. 1 shows the amino acid sequences of eight peptides from tryptic digestion of bovine BMP;

FIG. 2A and 2B show DNA and amino acid sequences of two exon-containing regions of the bovine BMP gene;

FIG. 3 shows the nucleotide sequence of bovine BMP cDNA and the deduced amino acid sequence of the precursor polypeptide;

FIGS. 4a through 4c -3 show the sequences of the exon-containing regions of the human BMP gene.

FIG. 5 shows the nucleotide sequence of human BMP and the deduced amino acid sequence of the precursor polypeptide.

DETAILED DESCRIPTION OF THE INVENTION

The BMP according to the present invention may be obtained, free of other osteoinductive associated factors, directly from bone sources, by preparative peptide synthesis using chemical methods (such as the Merrifield synthesis method) or by recombinant DNA technology.

As more particularly described in Example 1, BMP may be obtained from partially purified human, bovine, or other vertebrate bone extracts, by preparative gel electrophoresis and electroelution of the protein.

BMP nucleic acid sequences may be obtained by recombinant DNA methods, such as by screening reverse transcripts of mRNA, or by screening genomic libraries from any cell. The DNA may also be obtained by synthesizing the DNA using commonly available techniques and DNA synthesizing apparatus. Synthesis may be advantageous because unique restriction sites may be introduced at the time of preparing the DNA, thereby facilitating the use of the gene in vectors containing restriction sites not otherwise present in the native source. Furthermore, any desired site modification in the DNA may be introduced by synthesis, without the need to further modify the DNA by mutagenesis.

In general, DNA encoding the BMP may be obtained from human, bovine or other sources by constructing a cDNA library from mRNA isolated from vertebrate tissue; and screening with labeled DNA probes encoding portions of the human or bovine chains in order to detect clones in the cDNA library that contain homologous sequences; or by polymerase chain reaction (PCR) amplification of the cDNA (from mRNA) and subcloning and screening with labeled DNA probes; and then analyzing the clones by restriction enzyme analysis and nucleic acid sequencing so as to identify full-length clones and, if full-length clones are not present in the library, recovering appropriate fragments from the various clones and ligating them at restriction sites common to the clones to assemble a clone encoding a full-length molecule. Particularly preferred DNA probes are set forth in the accompanying examples. Any sequences missing from the 5' end of the BMP cDNA may be obtained by the 3' extension of the synthetic oligonucleotides complementary to BMP sequences using mRNA as a template (so-called primer extension), or homologous sequences may be supplied from known cDNAs derived from human or bovine sequences as shown in FIG. 3 or FIG. 5.

The practice of the present invention will employ, unless otherwise indicated, conventional molecular biology, microbiology, and recombinant DNA techniques within the skill of the art. Such techniques are explained fully in the literature. See e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. 1985); "Transcription And Translation" (B. D. Hames & S. J. Higgins eds. 1984); "Animal Cell Culture" (R. I. Freshney ed. 1986); "Immobilized Cells And Enzymes" (IRL Press, 1986); B. Perbal, "A Practical Guide To Molecular Cloning" (1984).

In describing the present invention, the following terminology will be used in accordance with the definitions set out below.

The term "osteoinductive associated factors" includes factors known in the art which are present in mammalian bone or other mammalian tissue and tend to co-purify with BMP or BMP activity. Such factors include, but are not limited to, proteins which have been isolated from bone having reported relative molecular weights by migration on SDS-PAGE of 34 KD, 24 KD, 18.5 KD, 17.5 KD, 16.5 KD, 14 KD (as cited in the U.S. Pat. No. 4,761,471), and 6 KD (reported by Price, P. A., et al., from *Prot. Natl. Acad. Sci.*, 73, pp. 1447–1451, 1976). All observed molecular weights are reported herein as relative molecular weight by migration on SDS-PAGE gel.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAT" boxes. Procaryotic promoters contain Shine-Dalgarno sequences in addition to the −10 and −35 consensus sequences.

A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N- terminal to the polypeptide, that communicates to the host cell to direct the polypeptide to the cell surface or secrete the polypeptide into the medium, and this signal peptide is clipped off by the host cell before the protein leaves the cell. Signal sequences can be found associated with a variety of proteins native to prokaryotes and eukaryotes. For instance, alpha-factor, a native yeast protein, is secreted from yeast, and its signal sequence can be attached to heterologous proteins to be secreted into the media (See U.S. Pat. No. 4,546,082, EPO 0 116 201, publication date 12 Jan. 1983;

U.S. patent application Ser. No. 522,909, filed 12 Aug. 1983). Further, the alpha-factor and its analogs have been found to secrete heterologous proteins from a variety of yeast, such as Saccharomyces and Kluyveromyces, (EPO 88312306.9 filed 23 Dec. 1988; U.S. patent application Ser. No. 139,682, filed 30 Dec. 1987, and EPO Pub. No. 0 301 669, publication date 1 Feb. 1989).

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 85% (preferably at least about 90%, and most preferably at least about 95%) of the nucleotides match over the defined length of the DNA sequences. Sequences that are substantially homologous can be identified in a Southern hybridization experiment under, for example, stringent conditions as defined for that particular system. Defining appropriate hybridization conditions is within the skill of the art. See, e.g., Maniatis et al., Supra; DNA Cloning, Vols. I & II, supra; Nucleic Acid Hybridization, Supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

An "antibody" is any immunoglobulin, including antibodies and fragments thereof, that binds a specific epitope. The term encompasses, inter alia, polyclonal, monoclonal, and chimeric antibodies.

For more about chimeric antibodies see U.S. Pat. Nos., 4,816,397 and 4,816,567.

The intron-free DNA provided by the present invention is novel, since it is believed that the naturally-occurring human and bovine genes contain introns. Hence, the term "intron-free" excludes the DNA sequences which naturally occur in the chromosomes of human or bovine cells. The present invention also encompasses the intron-free cDNA sequences derivable from the DNA sequences disclosed herein.

As more particularly described in the following examples, human and bovine cDNA libraries were initially probed for sequences encoding BMP sequences using labeled oligodeoxynucleotides whose sequences were based on a partial amino acid sequence determined from analysis of purified protein samples derived from bone described herein. However, it is realized that once being provided with intron-free DNA encoding human and bovine BMP and their leader sequences as described herein, one of ordinary skill in the art would recognize that other precisely hybridizing probes may be prepared from the described sequences in order to readily obtain the remainder of the desired human or bovine gene.

Vectors are used to simplify manipulation of the DNA which encodes the BMP polypeptide, either for preparation of large quantities of DNA for further processing (cloning vectors) or for expression of the BMP polypeptide (expression vectors). Vectors comprise plasmids, viruses (including phage), and integratable DNA fragments, i.e., fragments that are integratable into the host genome by recombination. Cloning vectors need not contain expression control sequences. However, control sequences in an expression vector include transcriptional and translational control sequences such as a transcriptional promoter, an optional operator sequence to control transcription, a sequence encoding suitable ribosome binding sites (for prokaryotic expression), and sequences which control termination of transcription and translation. The expression vector should preferably include a selection gene to facilitate the stable expression of BMP and/or to identify transformants. However, the selection gene for maintaining expression can be supplied by a separate vector in cotransformation systems using eukaryotic host cells.

Suitable vectors generally will contain replicon (origins of replication, for use in non-integrative vectors) and control sequences which are derived from species compatible with the intended expression host. By the term "replicable" vector as used herein, it is intended to encompass vectors containing such replicons as well as vectors which are replicated by integration into the host genome. Transformed host cells are cells which have been transformed or transfected with vectors containing BMP encoding DNA. The expressed BMP will be deposited intracellularly or secreted into either the periplasmic space or the culture supernatant, depending upon the host cell selected and the presence of suitable processing signals in the expressed peptide, e.g. homologous or heterologous signal sequences.

Suitable host cells are prokaryotes or eukaryotic cells. Prokaryotes include Gram negative or Gram positive organisms, for example *E. coli* or bacilli. Eukaryotic cells include yeast or higher eukaryotic cells such as established cell lines of mammalian origin.

Expression vectors for host cells ordinarily include an origin of replication, a promoter located upstream from the BMP coding sequence, together with a ribosome binding site, a polyadenylation site, and a transcriptional termination sequence. Those of ordinary skill will appreciate that certain of these sequences are not required for expression in certain hosts. An expression vector for use with microbes need only contain an origin of replication recognized by the host, a promoter which will function in the host and a selection gene.

An expression vector is constructed according to the present invention so that the BMP coding sequence is located in the vector with the appropriate regulatory sequences, the positioning and orientation of the coding sequence with respect to the control sequences being such that the coding sequence is transcribed and translated under the "control" of the control sequences (i.e., RNA polymerase which binds to the DNA molecule at the control sequences transcribes the coding sequence). The control sequences may be ligated to the coding sequence prior to insertion into a vector, such as the cloning vectors described above. Alternatively, the coding sequence can be cloned directly into an expression vector which already contains the control sequences and an appropriate restriction site. For expression of BMP in prokaryotes and yeast, the control sequences will necessarily be heterologous to the coding sequence. If the host cell is a prokaryote, it is also necessary that the coding sequence be free of introns (e.g., cDNA). If the selected host cell is a mammalian cell, the control sequences can be heterologous or homologous to the BMP coding sequence, and the coding sequence can either be genomic DNA containing introns or cDNA. Either genomic or cDNA coding sequences can be expressed in yeast.

Expression vectors must contain a promoter which is recognized by the host organism. Promoters commonly known and available which are used in recombinant DNA construction include the β-lactamase (penicillinase) and lactose promoter systems, a tryptophan (trp) promoter system and the tac promoter. While these are commonly used, other known microbial promoters are suitable.

In addition to prokaryotes, eukaryotic cells such as yeast are transformed with BMP encoding vectors. *Saccharomyces cerevisiae*, or common baker's yeast, is the most commonly used among lower eukaryotic host microorganisms. However, a number of other species are commonly available and useful herein. Yeast vectors generally will contain an origin of replication from the 2 micron yeast plasmid or an autonomously replicating sequence (ARS), a promoter, DNA encoding BMP, sequences for polyadenylation and transcription termination, and a selection gene.

Suitable promoter sequences in yeast vectors include the promoters for the glycolytic enzymes such as enolase, 3-phosphoglycerate kinase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which have the additional advantage of transcription controlled by growth conditions are the promoter regions for alcohol dehydrogenase 1 or 2, isocytochrome C, acid phosphatase, as well as enzymes responsible for maltose and galactose utilization.

Higher eukaryotic cell cultures may be used, whether from vertebrate or invertebrate cells, including insects, and the procedures of propagation thereof are known. See, for example, Tissue Culture, Academic Press, Kruse and Patterson, editors (1973).

Suitable host cells for expressing BMP in higher eukaryotes include: monkey kidney CVI line transformed by SV40 (COS-7, ATCC CRL 1651); baby hamster kidney cells (BHK, ATCC CRL 10); Chinese hamster ovary-cells-DHFR (described by Urlaub and Chasin, PNAS (USA) 77: 4216 (1980)); mouse Sertoli cells (TM4, Mather, J. P., *Biol. Reprod.* 23:243–251 (1980)); monkey kidney cells (CVI ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060652, ATCC CCL 51); rat hepatoma cells (HTC, M1, 54, Baumann, M., et al., *J. Cell Biol.* 85: 1–8 (1980)) and TRI cells (Mather, J. P., et al., *Annals N.Y. Acad. Sci.* 383: 44–68 (1982)). Commonly used promoters are derived from polyoma, adenovirus 2, and simian virus 40 (SV40). It will be appreciated that when expressed in mammalian tissue, the recombinant BMP may have higher molecular weight due to glycosylation. It is therefore intended that partially or completely glycosylated forms of BMP having molecular weights greater than 19 KD are within the scope of this invention as well as its unglycosylated forms.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also U.K. Pub. Nos. GB 2,121,054; GB 2,008,123; GB 2,007,675; and European Pub. No. 103,395. Preferred procaryotic expression systems are in *E. coli*.

Other preferred expression vectors are those for use in eucaryotic systems. An exemplary eucaryotic expression system is that employing vaccinia virus, which is well-known in the art. See. e.g., Macket et al. (1984) J. Virol. 49:857; "DNA Cloning, " Vol. II, pp. 191–211, supra; PCT Pub. No. WO 86/07593. Yeast expression vectors are known in the art. See, e.g., U.S. Pat. Nos. 4,446,235; 4,443,539; 4,430,428; see also European Pub. Nos. 103,409; 100,561; 96,491. Another preferred expression system is vector pHS1, which transforms Chinese hamster ovary cells. See PCT Pub. No. WO 87/02062. Mammalian tissue may be cotransformed with DNA encoding a selectable marker such as dihydrofolate reductase (DHFR) or thymidine kinase and DNA encoding BMP.

If wild type DHFR gene is employed, it is preferable to select a host cell which is deficient in DHFR, thus permitting the use of the DHFR coding sequence as marker for successful transfection in hgt⁻ medium, which lacks hypoxanthine, glycine, and thymidine. An appropriate host cell in this case is the Chinese hamster ovary (CHO) cell line deficient in DHFR activity, prepared and propagated as described by Urlaub and Chasin, 1980, *Proc. Nat. Acad. Sci.* (USA) 77: 4216. Expression vectors derived from baculovirus for use in insect cells are known and available in the art. See Lucklow and Summers, *Biotechnology,* 6, p. 47–55.

Depending on the expression system and host selected, BMP is produced by growing host cells transformed by an exogenous or heterologous DNA construct, such as an expression vector described above under conditions whereby the BMP protein is expressed. The BMP is then isolated from the host cells and purified. If the expression system secretes BMP into growth media, the protein can be purified directly from cell-free media. If the BMP protein is not secreted, it is isolated from cell lysates. The selection of the appropriate growth conditions and recovery methods are within the skill of the art.

The recombinantly made BMP is recovered from transformed cells in accordance with known procedures. Preferably, an expression vector will be used which provides for secretion of BMP from the transformed cells; thus the cells may be separated by centrifugation. The BMP typically is purified by general protein purification techniques, including, but not limited to, size exclusion, ion-exchange chromatography, HPLC, and the like.

Once a coding sequence for BMP has been prepared or isolated, it can be cloned into any suitable vector and thereby maintained in a composition of cells which is substantially free of cells that do not contain a BMP coding sequence (e.g., free of other library clones). Numerous cloning vectors are known to those of skill in the art. Examples of recombinant DNA vectors for cloning and host cells which they can transform include the various bacteriophage lambda vectors (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and Bacillus subtilis), pBD9 (Bacillus), pIJ61 (Streptomyces), pUC6 (Streptomyces), actinophage, φC31 (Streptomyces), YIp5 (Saccharomyces), YCp19 (Saccharomyces), and bovine papilloma virus (mammalian cells). See generally, DNA Cloning: Vols. I & II, supra; T. Maniatis et al., supra; B. Perbal, supra.

Alternatively the BMP may be made by conventional peptide synthesis, for instance, by using the principles of the Merrifield synthesis and using commercial automatic apparatus designed to employ the methods of the Merrifield synthesis. Peptides prepared using conventional peptide synthesis may be purified using conventional affinity chromatography, gel filtration and/or RP-HPLC.

FIG. 3 shows the nucleotide sequence of bovine BMP cDNA and the deduced amino acid sequence or the precursor polypeptide. The putative signal peptidase cleavage site is noted (↓). The cDNA sequence was obtained from a 830 bp Bgl II insert of bovine BMP cDNA clone #1, which was isolated from a calf liver cDNA library, as described below.

FIG. 5 shows the nucleotide sequence of human BMP cDNA and the deduced amino acid sequence of the precursor polypeptide. The putative signal peptidase cleavage site is noted (↓). The cDNA sequence was obtained from a 600 bp BamHI/HindIII insert of human BMP cDNA clone A6, which was isolated from a BMP/PCR human kidney cDNA library, as described below.

It is further intended from the nucleotides sequences in FIGS. 3 and 5 that BMP analogs are within the scope of the present invention. Analogs, such as fragments, may be produced, for example, by pepsin digestion of BMP. Other analogs, such as muteins, can be produced by standard site-directed mutagenesis of BMP coding sequences. Analogs exhibiting "BMP activity" may be identified by the in vivo and/or in vitro assays, preferably the in vitro cartilage inducing assay, *Methods of Enzymology*, 146, pp 294–312, (1987).

An example of a BMP analog is the yeast cleavage products produced in vivo from the full-length bovine or human BMP expression product. The processing of the bovine expression product results in two roughly 16 KD polypeptides, described in Example 9 below, and one or both of these analogs are referred to herein as the "16 KD yeast cleavage analog."

As mentioned above, a DNA sequence encoding BMP can be prepared synthetically rather than cloned. The DNA sequence can be designed with the appropriate codons for the BMP amino acid sequence. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292:756; Nambair, et al. (1984) *Science* 223:1299; Jay et al. (1984) *J. Biol. Chem.* 259:6311.

Synthetic DNA sequences allow convenient construction of genes which will express BMP analogs or "muteins". Alternatively, DNA encoding muteins can be made by site-directed mutagenesis of native BMP genes or cDNAs, and muteins can be made directly using conventional polypeptide synthesis.

Site-directed mutagenesis is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

A general method for site-specific incorporation of unnatural amino acids into proteins is described in Christopher J. Noren, Spencer J. Anthony-Cahill, Michael C. Griffith, Peter G. Schultz, (April 1989), Science, Vol 244, pp 182–188. This method may be used to create analogs with unnatural amino acids.

Preparations of BMP and its analogs may be assayed in vivo according to the method described by Urist, et al., *Methods in Enzymology* (D. Barnes and D. A. Sirbaska, eds.), vol. 146, pp. 294–312, Academic Press, New York (1987), and in vitro by the method of Sato and Urist, *Clin. Orthop.*, 183:180–187 (1984) as modified by Kawamura and Urist, *Dev. Biol.*, 130:435–442 (1988), all of which are incorporated by reference herein.

Substantially pure BMP, higher molecular glycosylated forms thereof, or active fragments thereof, or the nontoxic salts thereof, combined with a pharmaceutically acceptable carrier to form a pharmaceutical composition, may be administered to mammals, including humans, either intravenously, subcutaneously, percutaneously, intramuscularly or orally.

Such proteins are often administered in the form of pharmaceutically acceptable nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be affected.

Pharmaceutical compositions will usually contain an effective amount of BMP in conjunction with a conventional, pharmaceutically acceptable carrier. The dosage will vary depending upon the specific purpose for which the protein is being administered, and dosage levels in the range of about 0.1 µg to about 100 milligrams per Kg. of body weight may be used.

Implants of recombinant BMP, alone or when mixed with one or more osteoinductive associated factors may be used to initiate cartilage and bone growth. The implants can be time-release composition encapsulated, for instance, in liposomes or other time-release membranes, natural or synthetic, which are absorbable by the host subject. The BMP may be either human, bovine or any other mammalian form, or mixtures thereof. To initiate bone growth, BMP may be mixed with any combination of one or more other proteins, particularly, with one or more other proteins derived from bone. Such mixtures may initiate cartilage formation, followed by bone growth. Implants of BMP may be used to induce cartilage and bone growth in the quadriceps compartment.

The purification protocols, described in detail below, allow for the first time the purification of native BMP in sufficient quantity and at a high enough purity to permit accurate amino acid sequencing. The amino acid sequences derived from the purified BMP allow for the design of probes to aid in the isolation of native BMP nucleic acid sequence, or the design of synthetic nucleic acid sequences encoding the amino acid sequence of BMP, as well as allowing both diagnostic and therapeutic antibodies to BMP and its analogs to be produced for the first time. BMP DNA genes or fragments may also be utilized in a diagnostic test for identifying subjects having defective BMP-genes.

Specific anti-sera or monoclonal antibodies (described below) can be made to a synthetic BMP peptide having the sequence or fragments of the sequence of amino acid residues, such as those shown in FIGS. 3 or 5. Examples are the tryptic fragments shown in FIG. 1, and antibodies thereto can be used to immunoprecipitate any BMP present in a selected tissue, cell extract, or body fluid. Purified BMP from this source can then be sequenced and used as a basis for designing specific probes as described above. Antibodies to other regions that diverge from known BMP can also be used. Also useful as antigens are purified native or recombinant BMP.

Native, recombinant or synthetic BMP peptides (full length or subunits) can be used to produce both polyclonal and monoclonal antibodies. If polyclonal antibodies are desired, purified BMP peptide is used to immunize a selected mammal (e.g., mouse, rabbit, goat, horse, etc.) and serum from the immunized animal later collected and treated according to known procedures. Compositions containing polyclonal antibodies to a variety of antigens in addition to BMP can be made substantially free of antibodies which are not anti-BMP by immunoaffinity chromatography.

Monoclonal anti-BMP antibodies can also be readily produced by one skilled in the art from the disclosure herein. The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against BMP peptides can be screened for various properties; i.e., isotype, epitope, affinity, etc. Of particular interest are monoclonal antibodies that neutralize the activity of BMP. Such monoclonals can be readily identified in BMP activity assays. High affinity antibodies are also useful in immunoaffinity purification of native or recombinant BMP.

Antibodies to BMP (both polyclonal and monoclonal) forms described herein may be used to inhibit or to reverse various clinical indications of bone disease such as osteoporosis, osteoarthritis, etc. One therapeutic approach would be to treat the patient with an effective dose of anti-BMP antibodies through a conventional intravenous route. BMP antagonists or agonists, such as BMP muteins, could also be used in place of antibodies. These anti-BMP compositions may also be useful in detecting or inhibiting various forms of tumors, since some tumors are known to be induced by growth factors.

The determination of the appropriate treatment regimen (i.e., dosage, frequency of administration, systemic vs. local, etc.) is within the skill of the art. For administration, the antibodies will be formulated in a unit dosage injectable form (solution, suspension, emulsion, etc.) in association with a pharmaceutically acceptable parenteral vehicle. Such vehicles are usually nontoxic and nontherapeutic. Examples of such vehicles are water, saline, Ringer's solution, dextrose solution, and Hank's solution. Nonaqueous vehicles such as fixed oils and ethyl oleate may also be used. A preferred vehicle is 5% (w/w) human albumin in saline. The vehicle may contain minor amounts of additives, such as substances that enhance isotonicity and chemical stability, e.g., buffers and preservatives. The antibody is typically formulated in such vehicles at concentrations of about 1 µg/ml to 10 mg/ml.

Anti-BMP antibodies will also be useful in diagnostic applications. The present invention contemplates a method, particularly a diagnostic method, in which a sample from a human (or other mammal) is provided, and the amount of BMP is quantitatively measured in an assay. For example, employing anti-BMP antibodies in a quantitative immunoassay could be used to detect genetic deficiency in BMP. Antibody specific for BMP could be formulated into any conventional immunoassay format; e.g., homogeneous or heterogeneous, radioimmunoassay or ELISA. The various formats are well known to those skilled in the art. See, e.g., "Immunoassay" A Practical Guide" (D. W. Chan and M. T. Perlstein eds. 1987) the disclosure of which is incorporated herein by reference.

In general, production of recombinant BMP can provide compositions of that polypeptide substantially free of contaminating proteins. The ability to obtain high levels of purity is a result of recombinant expression systems which can produce BMP in substantial quantities vis-a-vis in vivo sources. Thus, by applying conventional techniques to recombinant cultures, BMP compositions can be produced that are substantially more pure than the compositions available from bone sources.

Purified BMP will be particularly useful as a tool in the design and screening of cartilage or bone growth inhibitors. First, milligram amounts of the material are obtainable according to the present invention. Milligram amounts are capable of crystallization to permit three dimensional studies using X-ray diffraction and computer analysis. This may permit deduction concerning the shape of the molecule, thus defining proper shapes for substances usable as inhibitors of the activity normally exhibited by BMP. Generally, antagonists have been peptides whose interactions with an a polypeptide, the activity of which is inhibited, are stabilized by modification of the "residues" participating in the peptide bond so as to enhance the ability of the peptide to interact specifically with the enzyme, receptor, or co-factor, such as osteoinductive associated factors in the case of BMP. Thus the peptide bond joins specifically chosen carboxylic acids and amines (not necessarily amino acids). These peptides are configured in a three dimensional array so as to complement the contours of the intended target. A similar lock and key spatial arrangement may result from molecules designed complementary to the surface contours of the BMP of the invention. It is understood that "surface" includes convolutions which may face inward, and specifically includes the active site. Furthermore, "complementary" is understood to mean that, in addition to spatial conformations which "fit" interactions between the protein and the molecule which matches its surface contours are attractive and positive. These interactions may be hydrogen bonding, ionic, or hydrophobic affinity.

Accordingly, the invention contemplates peptide antagonists and agonists (2–15 amino acids) to BMP which are characterized by three dimensional contours complementary to the three dimensional contours on the surface of recombinant BMP. By peptide in this context is meant that the antagonist or agonist contains carboxylic acid amide bonds. The carboxylic acid and amine participants need not be α-amino acids.

Second, even without the assistance of a three dimensional structure determination, purified BMP of the invention is useful as a reagent in screening BMP inhibitors in vitro as an ad hoc approach to evaluation. Impure BMP preparations currently available yield confusing data due to impurities. For example, contaminants which turn out to be themselves inhibitors, activators, or substrates for BMP may interfere with the evaluation. Thus, a substantial improvement in current screening techniques for BMP agonists and antagonists would be effected by the availability of the purified BMP protein.

It will be understood that this description and disclosure of the invention is intended to cover all changes and modifications of the invention which are within the spirit and scope of the invention. It is within the knowledge of the art to insert, delete or substitute amino acids within the amino acid sequence of a BMP without substantially affecting the calcification and bone growth inducing activity of the molecule. Thus, the invention includes such deletions, additions or substitutions. Furthermore, it is recognized that one skilled in the art could recombinantly produce such modified proteins.

The following examples are provided by way of illustration but are not intended to limit the invention in any way.

EXAMPLE 1

Purification of BMP From Bone

The BMP proteins of interest, partially purified from human (17 KD) and bovine (19 KD) sources as described by Urist, et al., *Proc. Nat. Acad. Sci. USA*, 81, 371–375 (1984), were further purified to homogeneity by preparative gel electrophoresis and electroelution (M. W. Hunkapiller, E. Lujan, F. Ostrander and L. E. Hood, *Methods in Enzymology*, 91:227–236 (1983)). This purification showed that the initial partially purified samples contained, in addition to the 19 KD BMP, other mammalian proteins at 34 KD, 22 KD, 14 KD and 6 KD. After precipitation with acetone (W. H. Konigsberg and L. Henderson, *Methods in Enzymology*, 91: 254–259 (1983)) and quantitation by amino acid analysis (B. A. Bidlingmeyer, S. A. Cohen and T. L. Tarvin, *Journal of Chromatography*, 336:93–104 (1984)), the material was reduced under denaturing conditions with 2-mercaptoethanol and cysteine residues were derivatized with 4-vinylpyridine (M. Friedman, L. G. Krull and J. F. Cavins, *Journal of Biological Chemistry*, 245:3868–3871 (1970)). After exhaustive dialysis to remove the denaturant, protein recovery was assessed by a repetition of amino acid analysis. The proteins were digested with TPCK-trypsin in the presence of 2M urea to generate unblocked peptide fragments suitable for sequence analysis (G. Allen, *Sequencing of Proteins and Peptides*, pages 51–62 (1981), Elsevier/North Holland Publishing Company, Amsterdam, Holland). Products of the digestion were resolved by reverse-phase high performance liquid chromatography using gradients of acetonitrile or acetonitrile/isopropanol in aqueous trifluoroacetic acid (J. E. Shively, *Methods of Protein Microcharacterization*, pages 41–87 (1986), Humana Press, Clifton, N.J.). Peptide fractions were subjected to automated Edman degradation using an Applied Biosystems 470A protein sequencer (M. W. Hunkapiller, R. M. Hewick, W. J. Dreyer and L. E. Hood, *Methods in Enzymology*, 91: 399–413 (1983)). The phenylthiohydantoin amino acid derivatives were identified by chromatography on an Applied Biosystems 120A PTH analyzer (M. W. Hunkapiller, *Applied Biosystems*, User Bulletin Number 14 (1985), Applied Biosystems, Foster City, Calif.).

EXAMPLE 2

RNA Isolation and Probe Synthesis

Cell culture. 293, an embryonic human kidney cell line obtained from the American Type Culture Collection (ATCC No. CRL 1573) was cultured in Dulbecco's modified Eagle's medium containing 10% fetal calf serum, 100 U/ml penicillin and 100 µg/ml streptomycin at 37° C. in 5% $CO_2$.

RNA isolation. RNA was isolated from calf liver (obtained from JR Scientific, Woodland, Calif.) by the guanidinium thiocyanate/CsCl method (Maniatis, T. Fritsch, E. F. and Sambrook, J. (1982) *Molecular Cloning: A Laboratory Manual* (Cold Spring Harbor Lab., Cold Spring Harbor, N.Y.) and Freeman, G. J., Clayberger, C., DeKruyff, R., Rosenblum, D. S. and Cantor, H. (1983) *Proc. Natl. Acad. Sci.: USA* 80: 4094–4098). Poly(A)$^+$ RNA was purified by a single fractionation over oligo(dT)-cellulose (Maniatis, T. Fritsch, E. F. and Sambrook, J. (1982) *Molecular Cloning: a Laboratory Manual* (Cold Spring Harbor Lab., Cold Spring Harbor, N.Y.)).

Oligonucleotide synthesis. Oligonucleotide adapters, primers and probes were synthesized by the phosphoramidite method with an Applied Biosystems (Foster City, Calif.) model 380A synthesizer, purified by polyacrylamide gel electrophoresis and desalted on a Waters SEP-PAK ($C_{18}$) cartridge.

(a) Adapters. A 14-mer oligonucleotide (5' CCTGTAGATCTCCG 3') and a 18-mer oligonucleotide (5' AATTCGGAGATCTACAGG 3') were synthesized and used as the EcoRI adapters for the cDNA library constructed in lambda ZAPII. The 14-mer was phosphorylated (Maniatis, T. Fritsch, E. F. and Sambrook, J. (1982) *Molecular Cloning: a Laboratory Manual* (Cold Spring Harbor Lab., Cold Spring Harbor, N.Y.)) and subsequently heated to 95° C. for 15 min. to inactivate polynucleotide kinase, prior to annealing with the 18-mer. These asymmetrically phosphorylated adapters also contain an internal BglII restriction enzyme site.

(b) PCR primers. Two 47-mer oligonucleotides were synthesized for PCR amplification of the complete coding region of human BMP cDNA from kidney cell line 293 mRNA and subsequent cloning into lambda ZAPII. The 5' sense primer (5' TCCGGACTCGAGGAATTC AAACAAT-CATGATTTCCAGAATGGAGAAG 3') and 3' antisense primer (5' GACTCGAGGAATTCGTCGACACCTCAAG-GCCGTTACTCAAA GTCAGT 3') are based on the sequence of the human gene exons 1 and 7, respectively. Both primers have 5' extensions (adapters) that contain several restriction enzyme sites.

Two additional sets of PCR primers/adapters were synthesized for amplifying bovine and human BMP cDNA clones (encoding only the mature protein) and subsequent cloning into pAB125, a plasmid containing the yeast α-factor leader sequence. The 5' sense primer (42-mer) for the human BMP cDNA (5' ACTACTGGT CTAGATAAAA-GATTCCCAGTGTACGACTACGAT 3') and the 5' sense primer (41-mer) for the bovine BMP cDNA (5' GGAAC-CCTCTCTAGATAAAAGATTCCCGGTGTATGACTATG 3') contain an XbaI site to facilitate ligation of the PCR amplified cDNA to the α-factor leader sequence. The 3' antisense primer (37-mer) for the human BMP cDNA (5' TCTTACCTGTCGACTATTACTCAAAGTCAGTATTTAT 3') and the 3' antisense primer (41-mer) for the bovine BMP cDNA (5' AATGGCCGTCGACTATCACTCAAAGC-CAGGGTTTACTCTTG 3') contain a SalI site directly after the stop codon.

(c) Probes. Oligonucleotide probes, based on the tryptic peptide sequences of bovine BMP, were synthesized for screening the bovine genomic library (Probes A–D) and are shown in FIG. 1. The actual probes are complementary to the sequences shown. The sequences of four additional BMP tryptic peptides were determined (E–H) and are also shown in FIG. 1. With some codons, two nucleotides were included at degenerate positions to increase the probability of a correct guess. At serine residues, two separate oligonucleotides for each probe (differing only at the serine codon) had to be synthesized due to the unique nature of the serine codon degeneracy.

Two partially overlapping 50-mer oligonucleotides, based on the bovine BMP exon 3 sequence, were synthesized for screening the calf liver cDNA library (Probe I) and are shown in FIG. 2a (underlined). Four oligonucleotide probes were synthesized to identify exons 1, 5, 6, and 7 of the human BMP gene (see Table 1). Probe BMP103 (5' CCAGTGGTTCATTCCAAGGA CAAATATCACCAA-CATCTTCATCGCCATCTTCTCCAT 3') is a 57-mer complementary to bovine BMP exon 1 coding sequences. Probe BMP104 (5' TCACTCAAAGCCAGGGTTTACTCT-TGCTCTGGGCC ACGGGTTCGAGTACCTTCTATT 3') is also a 57-mer complementary to bovine BMP exon 7 coding sequences. BMP 116 (5' GAGACCAAATA-GATAATTGTTTCTCCATTTATGAGATCC 3') is a 39-mer complementary to human BMP exon 5 coding sequences. BMP 117 (5' CAAGTGACCGATCATAAAA TTGT-TCACTTATGGACTCGTCTGAAATGAGA 3') is a 51-mer complementary to human BMP exon 6 coding sequences. A 26-mer oligonucleotide (5' TAGTCCCTCTGGAAGGCA-CATGTAGC 3') complementary to human BMP exon 3 coding sequences (Probe J) was synthesized for screening the human BMP/PCR cDNA library.

EXAMPLE 3

Construction and Screening of cDNA Libraries

Construction of the cDNA libraries. (a) Calf liver cDNA library. First strand cDNA was synthesized from calf liver poly(A)$^+$ RNA using conditions similar to Okayama and Berg [Okayama, H. and Berg, P. *Molec. and Cell Biol.*3:4094–4098 (1983)]. About 5 μg of poly(A)$^+$ RNA in 20 μl 5 mM Tris-hydrochloride (pH 7.5) was heated to 65° C. for 3 min., then quick cooled on wet ice and immediately adjusted (at room temperature) to contain 50 mM Tris-hydrochloride (pH 8.3 at 42° C.), 8 mM MgCl$_2$, 30 mM KCl, 10 mM dithiothreitol, 2 mM each of dATP, dGTP, dTTP and [α-$^{32}$P]dCTP(~300 cpm/pmol), 60 U RNasin, and 2.5 μg of oligo (dT)$_{12-18}$ (total volume 40 ml). The reaction was initiated by the addition of 50–60 U of cloned moloney murine leukemia virus reverse transcriptase and continued for 60 min. at 42° C. The second cDNA strand was synthesized by the method of Gubler and Hoffman [Gubler, U. and Hoffman, B. J. *Gene* 25:263–269 (1983)] as modified by Aruffo and Seed [Aruffo, A. and Seed, B. *Proc. Natl. Acad. Sci.*: USA 74:8573–8577 (1987)]. The ds cDNA was then ligated to asymmetrically (hemi) phosphorylated EcoRI adapters (see oligonucleotide synthesis) as described by Aruffo and Seed, supra, phosphorylated with T$_4$ polynucleotide kinase (Maniatis, et al., supra), adjusted to 0.5M NaCl, 25 mM EDTA and heated at 75° C. for 15 min. to inactivate the polynucleotide kinase. The ds cDNA was separated from unligated adapters by chromatography on Biogel A-15 m and recovered by ethanol precipitation. cDNA was ligated to EcoRI-cut lambda ZAPII (Stratagene) with T$_4$ DNA ligase (New England Biolabs) as described by supplier, but included 15% polyethylene glycol (PEG) 8000 (Sigma), a modification described by Pheiffer and Zimmerman [Pheiffer, B. H. and Zimmerman, S. B. *Nucl. Acids. Res.* 11:7853–7871 (1983)]. The ligated DNA was recovered by centrifugation (12,000 ×g), washed with chloroform, dried, resuspended in 4 μl water and incubated with an in vitro packaging extract (Stratagene) according to supplier. Recombinant phage was propagated in *E. coli* XLI-Blue (Stratagene).

(b) BMP primed-PCR amplified (BMP/PCR) human kidney cDNA library. The PCR reactions were performed as described by the suppliers of the PCR kit (Perkin/Elmer/Cetus). Two synthetic 47-mer oligonucleotide primers whose sequences were derived from exon 1 (sense primer) and 7 (antisense primer) of the human BMP gene and contained restriction site adapters suitable for cloning were used at a final concentration of 1 μM each. The PCR primers flank the complete coding region of hBMP mRNA. The template cDNA was synthesized from 2.5 μg of embryonic human kidney cell line 293 poly(A)$^+$ RNA. The conditions of cDNA synthesis were identical to the above (Part A) except that the reaction volume was 20 μl. The cDNA was fractionated on Biogel A-15 m, also as above, recovered by ethanol precipitation and resuspended in 100 μl of sterile water. 1–10 μl of cDNA template were used for each PCR reaction. 40 cycles of PCR were performed in a Perkin/Elmer/Cetus DNA thermal cycler. Each cycle consisted of a 94° C., 1 min. denaturation step, a 55° C., 2 min. annealing step and a 72° C., 3 min. extension step. The extension step in cycle 40 was 15 min. instead of 3 min. Samples were extracted once with phenol/chloroform/IAA (1:1:0.04) once with chloroform/IAA (24:1), recovered by ethanol precipitation, digested with EcoRI and fractionated by electrophoresis on a 7% acrylamide, 1×TBE gel. DNA migrating between 400–800 b.p. was excised from the gel, purified by passage over an Elutip-d column, ligated to Eco-RI cut lambda ZAPII, packaged and propagated as above (Part A).

Screening of the libraries. (a) Bovine genomic library. Approximately 10$^6$ recombinant phage from a bovine genomic library (Clontech) were plated (20,000 phage/137 mm dia plate) in *E. coli* LE392, and grown for 5–6 hours at 37° C. The phage were transferred onto nitrocellulose filters (Millipore, HATF137) processed according to Benton and Davis (8) and screened with probe A (FIG. 1). The probes were end-labeled with $T_4$ polynucleotide kinase and ($\delta$632-p) ATP (1) to a specific activity of $1-2\times10^8$ cmp/µg. The filters were prehybridized for 1–2 h at 37° C. in 5×SSC (1×SSC=0.15M sodium chloride/0.015M sodium citrate, pH 7), 5×Denhardt's solution (1×Denhardt's solution=0.02% polyvinylpyrrolidone/0.02% Ficoll/0.02% bovine serum albumin), 10% dextran sulfate, 50 mM sodium phosphate pH 6.8, 1 mM sodium pyrophosphate, 0.1% $NaDodSO_4$ and 50 µg/ml denatured salmon sperm DNA. Labeled probe was added to a concentration of $10^6$ cpm/ml and hybridization was continued overnight at 37° C. with gentle shaking. The filters were washed in 2×SSC, 0.1% $NaDodSO_4$ at 55° C., and exposed to Kodak XAR-2 film with a DuPont Lightning Plus intensifying screen overnight at −80° C. After development, the probe was removed from the filters by washing in 0.1×SSC, 0.1% $NaDodSO_4$ at 65° C. One set of filters was then hybridized with probe B (FIG. 1) and washed and exposed as above. Areas of plaques giving signals with probes A and B were picked, replated, transferred onto nitrocellulose in quadruplicate, amplified according to Woo (21) and screened with probes A–D (FIG. 1) (one probe per filter). Filters were washed and exposed to film as above. A plaque giving signals with three (A–C) of the four probes was purified by an additional round of plating and screening.

(b) Calf liver cDNA library. Approximately 192,000 recombinant phage were plated (16,000 phage/137 mm dia plate) in *E. coli* XL1-Blue, processed as above and screened with *E. coli* probe I (FIG. 2*a*). The probe was labeled with DNA polymerase I (Klenow fragment) and ($\alpha^{32}$-P)-d CTP (9) to a specific activity of $2\times10^9$ cpm/µg. The filters were screened as above (a) but with the following changes. (1) The hybridization solution contained 40% formamide and (2) the filters were washed in 2×SSC, 0.1% $NaDodSO_4$ at 65° C.

(c) Human genomic library. Approximately $10^6$ recombinant phage from a human genomic library (Stratagene) were plated (50,000 phage/plate) in *E. coli* LE392, processed and screened with the 780 bp BglII insert of bBMP cDNA#1 (FIG. 3). The probe was labeled (9) and the filters were hybridized as above (see calf liver cDNA library). The filters were washed in 2×SSC, 0.1% $NaDodSO_4$ at 60° C. Positive plaques were purified by replating and rescreening.

(d) (BMP/PCR) human kidney cDNA library. Approximately 1000 recombinant phage were plated (500 mm dia plate) in *E. Coli*. XL1 Blue, processed, hybridized with probe J (FIG. 4*b*, underlined) and washed as in (a). Positive plaques were purified by replating and rescreening.

EXAMPLE 4

Plasmid and Phage DNA Isolation, Subcloning, Sequencing and Analysis

Plasmid DNA was isolated by the alkaline lysis method (Maniatis, et al., supra) and lambda DNA was isolated by a phage miniprep procedure described by Jones and Rawls, [Jones, K. W. and Rawls, *J. M Genetics* 120:733–742 (1988)].

Bluescript SK(−) plasmids containing BMP cDNA were released from lambda ZAP by the M13 rescue/excision protocol described by the supplier (Stratagene). BMP gene fragments were released from the EMBL3 lambda vector by SalI or other appropriate restriction enzyme digestions (see FIG. 2 and Table 1). BMP cDNA inserts were excised from the Bluescript SK(−) vector by a BglII (bBMP cDNA) or a BamHI/HindIII (hBMP cDNA) digestion. The DNA fragments were purified by polyacrylamide or agarose gel electrophoresis (Maniatis, et al., Supra) and passage over an Elutip-d column (Schleicher and Schuell) and were then subcloned into pUC 19 or M13 sequencing vectors [Yamisch-Perron, C., Vieira, J. and Messing, J., *Gene* 33:103–119 (1985)]. DNA sequencing was performed by the dideoxy chain termination method (Sanger, F., Nicklen, S. and Coulson, A/ R., *Proc. Natl. Acad. Sci.* USA 74:5463–67 (1977)] using M13 primers as well as specific internal primers. Ambiguous regions were resolved using 7-deaza-2-deoxyguanidine-triphosphate [Barr, P. J., Thayer, R. M., Laybourn, P., Najarian, R. C., Seela, F., and Tolan, D., *Biotechniques* 4:428–32 (1986)] and sequenase (U.S. Biochemicals).

Northern blot analysis. Poly(A)$^+$ RNA was fractionated on a 1.4% agarose gel in the presence of formaldehyde (Lehrach, H., Diamond, D., Wozney, J. M. and Boedtker, H., *Biochemistry* 16:4743–51 (1977)] and directly transferred to nitrocellulose according to Thomas (Thomas, P., *Proc. Natl. Acad. Sci.* USA 77:5201–5 (1980) ].

Filters were hybridized with probe I or bBMP cDNA #1 and washed as previously described above in screening of the libraries, section B.

Southern blot analysis. Genomic blots: 10 µg of human, bovine and mouse genomic DNA (Clontech) was digested with EcoRI, fractionated on a 0.7% agarose gel and transferred to nitrocellulose (Maniatis, et al., supra). Hybridization and washing were identical to those described under "Northern blot analysis." Clone and PCR blots: DNA from genomic clones, cDNA clones or PCR reactions were digested with various restriction enzymes, fractionated on 1% agarose gels and transferred to nitrocellulose (Maniatis, et al., supra).

EXAMPLE 5

Expression of Bovine and Human BMPs in Yeast

The PCR primers described in detail above were used to generate DNA sequences with Xba-1 and Sal-1 restriction sites for direct in-frame cloning into pAB125, a vector containing the e-factor leader (described in EPO Pub. No. 0 116 201, published 22 Aug. 1984) sequence fused to the ADH2/GAPDH promoter (described in a copending U.S. patent application Ser. No. 760,197, filed 29 Jul. 1985). The resulting promoter/leader/gene cassettes were excised with BamH1 and Sal-1 and cloned into the yeast expression vector pBS24.1. The plasmid pBS24.1 is a derivative a pBS24 which is described in copending U.S. patent application Ser. No. 138,894, filed 24 Dec. 1987. The BamHI-SalI vector fragment of pBS24 was ligated to a 65 base pair human basic FGF BamHI-SalI fragment to create pBS24.1. This 65 base pair fragment will be replaced by the BamHI-SalI promoter/leader/BMP cassettes which are ligated into pBS24.1 The resulting plasmids pBS24bBMP and pBS24hBMP were used to transform yeast strain AB110 with genotype Mata, ura3-52, leu2-04 or both leu2-3 and leu2-112, pep4-3, his4-580, cir°, under leucine selection media, such as the synthetic complete media without leucine in *Methods in Yeast Genetics*, Cold Spring Harbor Laboratories, 1986, F. Sherman, G. R. Fink and J. B. Hicks. For induction of expression, cells were grown for 48 h the uracil deficient media below:

20 g Casamino Acids
5 g Ammonium Sulfate
1 g Potassium Phosphate
0.5 g Magnesium Sulfate
0.1 g Sodium Chloride
0.1 g Calcium Chloride
0.04 ml Trace Elements Mixture
41 1 2% Sodium Molybdate
0.015 g Vitamin Mix
0.03 g Pantothenate
0.03 g Inositol
70 ml 50% Glucose
q.s. to a 900 ml and pH to 6.0
q.s to 1000 ml
Trace Elements Mixture
5 g Boric Acid
0.4 g Cupric Sulfate
1 g Potassium Iodide
2 g Ferric-Chloride
4 g Manganese Sulfate
2 g Sodium Molybdate
4 g Zinc Sulfate
q.s. to 1000 ml and sterilize by filtration.
Vitamin Mix
3 g Myo-Inositol
3 g Thiamine
3 g Pyridoxine
3 g Calcium Pantothenate
0.2 g Biotin
2 g p-Aminobenzoic Acid
2 g Riboflavin
0.2 g Folic acid
3 g Niacin Yeast cells were removed from the culture media by centrifugation and the proteins in the supernatants analyzed after precipitation with 10% trichloroacetic acid/deoxycholate (0.4 mg/ml). The pellets were washed with acetone and loaded onto 15% SDS-polyacrylamide gels together with appropriate controls. Proteins were visualized by Coomassie blue staining. A samples of S. cerevisiae strain AB110 containing pBS24.1bBMP or pBS24.1hBMP were deposited with the ATCC on 1 Jun. 1989 under Accession Nos. 20949 and 20950.

EXAMPLE 6

Recombinant Bovine BMP Purification

Medium was removed from yeast cells by centrifugation, and concentrated approximately ten fold. The pH was adjusted to 4.5 and the concentrate diluted to a conductivity below 5 mS/cm. This was applied to Fast Flow S ion-exchange resin (Pharmacia) pre-equilibrated with 50 mM sodium acetate, 1 mM EDTA, 1 mM PMSF (pH 4.5). The column was washed with one volume of the above buffer and eluted using a 0–1M sodium chloride gradient in the above buffer. The 19 KD and 16 KD proteins eluted at a conductivity of 5–25 mS/cm, as confirmed by SDS-PAGE. The fractions containing predominantly the 19 KD protein were pooled, adjusted to pH 7.5 and 4.5M with respect to urea, concentrated, and applied to an S-100 sizing column in 4M urea, 100 mM Tris/HCl, 1 mM EDTA, 1 mM PMSF (pH 7.5). Fractions containing 19 KD and 16 KD proteins were identified by SDS-PAGE, pooled separately, concentrated and dialyzed against water, prior to lyophilization.

EXAMPLE 7

ASSAY FOR BMP ACTIVITY

Samples of purified recombinant BMP were added to CMRL-1066 (GIBCO) culture medium containing fetal rat midbelly triceps brachii muscle fragments. Connective tissue outgrowths were cultured on a substratum of BMP-free matrix from the diaphyses of long bones of adult male Sprague-Dawley rats. This assay is detailed more fully by Kawamura and Urist, Developmental Biology, 330, 435–442 (1982). The inductive activity is measured by [$^3$H]thymidine incorporation into DNA, [$^{35}$S]sulfate incorporation into glycosaminoglycans and confirmation of chondrogenesis (cartilage formation) by histology. Recombinant BMP was tested at concentrations of 200 ng/ml to 5 μg/ml in the 2 ml culture system. The, same level of positive results was observed with recombinant BMP as was previously noted with native BMP at equivalent concentrations. Higher [$^3$H]thymidine and [$^{35}$S]sulfate incorporation and new cartilage and chondrocytes were observed in the recombinant BMP induced cultures. No cartilage or chondrocytes were seen in control cultures without recombinant BMP.

EXAMPLE 8

Isolation and Analysis of the BMP gene and cDNA

I. The Bovine BMP gene.

Probes A and B (FIG. 1) were used to isolate 1 strongly and 7 weakly hybridizing clones from 10$^6$ recombinants of a bovine genomic library. The one strongly hybridizing clone (29-bg-3) was subjected to a second round of screening with probes A–D (FIG. 1). Three of the probes (A–C) hybridized to 29-bg-3. Southern blot analysis of purified 29-bg-3 DNA localized probes A and B to a 1.9kb EcoRI fragment and probe C to a 1.2kb EcoRI-SalI fragment. Both fragments were sequenced and shown to contain regions, in the top reading frame, encoding their respective tryptic peptides (FIG. 2; boxed amino acids). Interestingly, tryptic peptide D was also present but was split between two exons, thus explaining the lack of hybridization with probe D. Intron-Exon boundaries conform to the GT-AG rule and are denoted by vertical lines. Additional bovine BMP exons were not isolated. Attempts were directed at isolating a bovine BMP cDNA clone using as a probe exon sequences derived from the bovine BMP gene.

II. The Bovine BMP cDNA

Northern blot analysis of poly(A)$^+$ RNA from several bovine tissues using probe I revealed calf liver as a good source of bovine BMP mRNA (data not shown). Probe I was then used to isolate putative bovine BMP cDNA clones from a calf liver cDNA library. Two clones (#1 and #7) were sequenced, and shown to contain identical overlapping sequences as well as the expected encoded tryptic peptides (A–D) (FIG. 3). The additional BMP tryptic peptides (E–H, FIG. 1) were also found encoded in the bovine BMP cDNA.

III. The Human BMP gene

Northern blot analysis of poly(A)$^+$ RNA from several human tissues and cell lines, including liver, kidney and osteosarcoma, (using bovine BMP cDNA #1 as a probe) failed to detect human BMP. However, a Southern blot, performed under identical hybridization and wash conditions detected human BMP gene fragments (data not shown).

Based on the Northern and Southern results, the following strategy was adopted to (1) clone and sequence the human BMP gene, then (2) identify a tissue source of human BMP mRNA by PCR amplification (using human BMP based primers; BMP/PCR cDNA) and Southern blot analysis of the products 3) clone and isolate the PCR generated human BMP cDNA.

Bovine BMP cDNA #1 was used as a probe to isolate 7 strongly and 5 weakly hybridizing clones from $10^6$ recombinants of a human genomic library. Southern blot analysis of purified DNA from 11 of the 12 clones identified two hybridizing HindIII fragments (1.7 kb and 2.0 kb) common to three clones HG4, 5 and 9. The 1.7 kb and 2.0 kb HindIII fragments from HG9 were sequenced and shown to have a 63.4% and 62.2% amino acid homology to the bovine BMP exons shown on FIG. 2A and 2B respectively. Table 1 summarizes these results as well as the Southern blot results for the remaining human BMP exons. The sequence of the exon-containing region of each subclone is shown in FIG. 4a–c. The 5' end of exon 1 (Cap site) and the 3' end of exon 7 (poly(A)$^+$ addition site) are unknown. The intron/exon boundaries follow the GT-AG rule and are denoted by vertical lines. The DNA was translated in all three reading frames. The middle and top frames contain the correct amino acids for exons 1–6 and exon 7, respectively (boxed).

IV. The Human BMP cDNA

Kidney (cell line, 293) was identified as a source of hBMP mRNA by PCR amplification and Southern blot analysis. $10^3$ recombinants of a cDNA library made from the hBMP/PCR cDNA, were screened with probe J (human exon 3 probe) and 12 putative hBMP cDNA clones were isolated. Agarose gel electrophoresis following a BamHI/HindIII digestion of the clones showed that each clone contained either a 700 bp or a 600 bp cDNA insert. DNA sequencing revealed that the 700 bp species was the expected full length human BMP cDNA (FIG. 5) while the 600 bp species was a truncated human BMP cDNA, missing exon 2 (not shown). This shorter cDNA species most likely represents an aberrantly spliced, non-functional mRNA since a translational frameshift occurs at the newly formed exon 1/exon 3 junction resulting in a premature termination codon.

EXAMPLE 9

Analysis of Human and Bovine BMPs Expressed in Yeast hBMP is expressed in yeast as a mixture of three approximately 17 KD proteins, whereas bBMP is expressed as a mixture of 3 species with molecular weights of 19 KD and a 16 KD doublet. The size heterogeneity is most probably a result of processing of each BMP by yeast encoded enzyme(s) during secretion. Amino-terminal amino acid sequencing of the bBMP mixture gave a single amino terminus (Phe), indicating that the processing occurs in the carboxyl region of the protein, yielding the 16 KD yeast cleavage analogs. Several paired basic amino acid residues in this region are likely candidates as proteolysis sites during secretion. This observation, together with the fact that each BMP cDNA encodes a putative protein product of molecular weight greater than 20 kD, also underscores the possibility that BMP, in vivo, is the product of proteolytic processing from a larger precursor.

TABLE 1

A Summary of the Southern Blot Results Identifying Human BMP Exon-Containing DNA from Genomic Clones.

| Exon | Restriction Fragment[1] | | Genomic Clone[2] | Probe[4] |
| --- | --- | --- | --- | --- |
| | Size (kb) | Enzyme | | |
| 1 | 0.6 | Pst I | Hg 4[3] | BMP 103 |
| 2 | 0.6 | Pst I | HG 4[3] | hBMP cDNA |
| 3 | 1.7 | Hind III | HG 9 | bBMP cDNA |
| 4 | 2.0 | Hind III | HG 9 | bBMP cDNA |
| 5 | 0.4 | Bgl II | HG 5 | BMP 116 |
| 6 | 3.0 | Bgl II | HG 5[3] | BMP 117 |
| 7 | 1.1 | Bgl II | HG 5 | BMP 104 |

[1]Exon-containing DNA restriction fragment.
[2]Genomic clone from which restriction fragment was derived.
[3]Exon 1 and 2 DNA's were obtained from a 7 kb Sal I fragment of HG 4 subcloned into pUC 19. Both exons were found on the same Pst I fragment, but identified with different probes. Exon 6 was obtained from a 15 kb Sal I insert of HG5 subcloned into pUC19.
[4]Probe used to identify exon-containing DNA restriction fragment. Probes are described in "Oligonucleotide Synthesis" section of Materials and Methods. Hybridization and washing conditions are described under Example 3 in the "Screening of the libraries (c) human genomic library" section of the examples.

We claim:

1. An isolated DNA molecule comprising a nucleotide sequence that encodes a polypeptide, wherein the polypeptide comprises an amino acid sequence selected from the group consisting of an amino acid sequence as shown in FIG. 3, comprising amino acid residues numbered 1 through 180, and an amino acid sequence as shown in FIG. 5, comprising amino acid residues numbered 1 through 182.

2. The DNA molecule according to claim 1, wherein the amino acid sequence of the polypeptide is the amino acid sequence as shown in FIG. 5.

3. The DNA molecule according to claim 1, wherein the amino acid sequence of the polypeptide is the amino acid sequence as shown in FIG. 3.

4. The DNA molecule according to claim 1, further comprising a second nucleotide sequence that encodes a signal sequence for secretion of the polypeptide.

5. The DNA molecule according to claim 4, wherein the second nucleotide sequence encodes an N-terminal yeast alpha-factor signal sequence.

6. A vector comprising the DNA molecule according to claim 1.

7. A recombinant host cell comprising a vector according to claim 6.

8. A method of producing recombinant mammalian bone morphogenetic protein (BMP):

(a) providing a cell that comprises an isolated DNA molecule, wherein said DNA molecule comprises a DNA sequence comprising (i) transcriptional and translational control sequences functional in said cell, and (ii) a heterologous coding sequence under the control of said transcriptional and translation sequences, wherein the heterologous coding sequence encodes a polypeptide wherein the polypeptide comprises an amino acid sequence selected from the group consisting of an amino acid sequence as shown in FIG. 3, comprising amino acid residues numbered 1 through 180, and an amino acid sequence as shown in FIG. 5, comprising amino acid residues numbered 1 through 182;

(b) growing said cell under conditions whereby said polypeptide is expressed; and (c) isolating said polypeptide from said cell.

9. The method of claim 8, wherein the amino acid sequence of the polypeptide is the amino acid sequence as shown in FIG. 5.

10. The method of claim 8, wherein the amino acid sequence of the polypeptide is the amino acid sequence as shown in FIG. 3.

11. The method of claim 8, wherein the cell is a microorganism.

12. The method of claim 8, wherein the cell is a yeast cell.

13. The method of claim 8, wherein the cell is a *E. coli* cell.

14. The method of claim 8, wherein the isolated DNA molecule further comprises a second DNA sequence that encodes a signal sequence, wherein the signal sequence is disposed at the N-terminal of said polypeptide for secretion of the polypeptide.

15. The method of claim 14, wherein the cell is a yeast cell and said signal sequence is a yeast alpha-factor signal sequence.

16. An isolated DNA molecule comprising a nucleotide sequence that encodes a peptide selected from the group consisting of peptides A, B, C, D, of FIG. 1.

17. An isolated DNA molecule comprising a nucleotide sequence selected from the group consisting of Exon 3 of FIG. 2A and Exon 4 of FIG. 2B.

18. An isolated DNA molecule comprising a nucleotide sequence selected from the group consisting of Exon 1 of FIG. 4*a*., Exon 2 of FIG. 4*a*., Exon 3 of FIG. 4*b*., Exon 4 of FIG. 4*b*., Exon 5 of FIG. 4*c*., Exon 6 of FIG. 4*c*., and Exon 7 of FIG. 4*c*.

\* \* \* \* \*